US006171107B1

(12) United States Patent
Milne

(10) Patent No.: US 6,171,107 B1
(45) Date of Patent: Jan. 9, 2001

(54) MAGNETIC ADHESIVE AND REMOVAL APPARATUS AND METHOD

(76) Inventor: Robert H. Milne, 700 NE. Multnomah, Suite 840, Portland, OR (US) 97232

(*) Notice: Under 35 U.S.C. 154(b), the term of this patent shall be extended for 0 days.

(21) Appl. No.: 09/263,473

(22) Filed: Mar. 5, 1999

(51) Int. Cl.$^7$ .......................... A61C 13/235; B32B 31/28

(52) U.S. Cl. ........................ 433/189; 433/180; 156/272.4

(58) Field of Search .................................... 433/189, 180, 433/183; 156/272.4

(56) References Cited

U.S. PATENT DOCUMENTS

| | | | | |
|---|---|---|---|---|
| 3,512,382 | * | 5/1970 | Check et al. . | |
| 3,730,804 | * | 5/1973 | Dickey | 156/272.4 |
| 4,035,547 | * | 7/1977 | Heller, Jr. et al. | 156/272.4 |
| 4,202,097 | * | 5/1980 | Erlich-Deguemp | 433/189 |
| 4,214,366 | | 7/1980 | Laban . | |
| 4,508,507 | | 4/1985 | Jackson . | |
| 4,530,663 | | 7/1985 | Portnoy . | |
| 4,693,686 | | 9/1987 | Sendax . | |
| 4,880,383 | | 11/1989 | Weber . | |
| 4,993,950 | | 2/1991 | Mensor, Jr. . | |
| 4,997,372 | | 3/1991 | Shiner et al. . | |
| 5,013,243 | | 5/1991 | Tanaka et al. . | |
| 5,123,989 | * | 6/1992 | Horiishi et al. | 156/272.4 |
| 5,254,006 | | 10/1993 | Yamada . | |
| 5,302,122 | | 4/1994 | Milne . | |
| 5,460,635 | | 10/1995 | Koch et al. . | |
| 5,611,689 | | 3/1997 | Stemmann . | |
| 5,636,990 | | 6/1997 | Stemmann . | |
| 5,678,998 | | 10/1997 | Honkura et al. . | |
| 5,679,119 | | 10/1997 | Freeman et al. . | |
| 5,704,788 | | 1/1998 | Milne . | |
| 5,788,493 | | 8/1998 | Tanaka et al. . | |
| 5,833,795 | * | 11/1998 | Smith et al. | 156/272.4 |
| 5,871,357 | * | 2/1999 | Tseng | 433/189 |
| 5,890,892 | * | 4/1999 | Lemchen . | |
| 5,944,529 | * | 8/1999 | Rappold . | |

* cited by examiner

*Primary Examiner*—Ralph A. Lewis
(74) *Attorney, Agent, or Firm*—Dellett and Walters

(57) ABSTRACT

An adhesive for bonding items includes magnetic particles dispersed therein. Removal is enhanced by applying varying magnetic fields near the adhesive. Magnetic locking elements are biased to engage a catch portion. Removal is effected by urging the magnetic elements out of the catch portion by application of magnetic fields of opposite polarity.

18 Claims, 3 Drawing Sheets

MAGNETIC ADHESIVE AND REMOVAL APPARATUS AND METHOD

BACKGROUND OF THE INVENTION

This invention relates to methods, compounds and devices for adhering items together and more specifically, to adhesive and removal methods and apparatus for securing and removing secured items such that they are removed through the application of magnetic fields.

Throughout daily life, there are many occasions requiring that two or more items be secured to one another. For example, in the field of dentistry, there are several ways to permanently secure prosthodontics such that they maintain a proper spatial relationship to either part of an existing tooth or a dental implant. A more commonly employed technique involves the use of some form of dental cement placed between the tooth or implant and the prosthodontic device. Dental cement chemistry is a complex science and the actual method of "affixation" varies. In some types of dental cement, the cement flows into surfaces characterized by micro roughness on the items being cemented. These micro rough surfaces hold onto the cement once the cement has set, thus holding the items together.

While these cements allow for a firm bond, removing the cemented prosthodontics can be difficult, time consuming, and uncomfortable for both the patient and the dentist. Additionally, physical forces generated in conventional removal processes can damage the underlying tooth or implant. For this reason many affixed prosthodontic devices are infrequently removed for examination, except when dental problems arise.

In the field of prosthodontics, it has been known to employ magnets for securing items together. However, this use of magnetism has hereto been restricted to applications involving affixation between two prosthodontic devices such as an implant and a crown, bridge, or denture. One problem with prior magnetic affixation, typically using a magnet and a ferromagnetic material to which the magnet holds (or another magnet), is the lack of holding power to prevent relative movement between the affixed components. U.S. Pat. No. 4,693,686 (Sendax) incorporates pairs of magnets with one magnet positioned within an implant and the other magnet positioned within a prosthodontic device. The attractive forces between these magnets secure the prosthodontics. U.S. Pat. No. 4,214,366 (Laban), U.S. Pat. No. 5,788,493 (Tanaka et al), U.S. Pat. No. 5,678,998 (Honkura et al), U.S. Pat. No. 5,611,689 (Stemmann), and U.S. Pat. No. 4,997,372 (Shiner et al) all use variations in design of similar concepts. Other patents such as U.S. Pat. No. 5,636,990 (Stemmann), U.S. Pat. No. 5,254,006 (Yamada), and U.S. Pat. No. 5,013,243 (Tanaka et al) function in similar ways, but use the attractive forces between a single magnet and a ferromagnetic material to secure prosthodontic devices in position.

SUMMARY OF THE INVENTION

The present invention relates to a method, compound and apparatus for securing two items together and magnetically assisted separation of the secured items. An adhesive with magnetic particles therein is employed to secure two items together, and, should it be desired to separate the secured items, applied magnetic fields are used to assist in the removal or separation of the secured items. In this manner, the affixation strength of conventional methods is maintained yet removal is considerably simplified, with less potential for damage to the underlying structures of the secured items.

In a particular embodiment, the method, adhesive compound and apparatus are employed in the field of affixing prosthodontic devices by applying a layer of dental cement between the two surfaces of the mating devices. Accordingly, an embodiment of the invention comprises a cement that contains magnetic particles, suitably homogeneously interspersed within the cement. A feature of this embodiment is the ability of the cement to be broken up by the "shaking" of the magnetic particles in response to the application of an alternating electromagnetic field.

In another aspect of the invention, outwardly biased arms in a first portion engage corresponding catches in a second portion. The arms include magnetic portions thereon, whereby application of magnetic fields of proper polarity will urge the arms inwardly against the bias, and out of the catch portions, to enable separation of the first and second portions. However, in absense of the proper magnetic fields, the items are held together.

Accordingly, it is an object of the present invention to provide an improved adhesive for adhering items together.

It is a further object of the present invention to provide an improved an improved adhesive enabling easier separation of secured items when desired.

It is another object of the present invention to provide an improved adhesive for securing prosthodontic devices that enables easier removal.

Another object of the invention is to provide and improved apparatus for affixing prosthodontic devices together.

It is a further object of the present invention to rovide an improved apparatus and method for removing prosthodontic devices.

It is yet another object of the present invention to provide an improved magnetic apparatus and method that enables quick and simple separating of prosthodontic devices.

The subject matter of the present invention is particularly pointed out and distinctly claimed in the concluding portion of this specification. However, both the organization and method of operation, together with further advantages and objects thereof, may best be understood by reference to the following description taken in connection with accompanying drawings wherein like reference characters refer to like elements.

DETAILED DESCRIPTION

Figure 1:
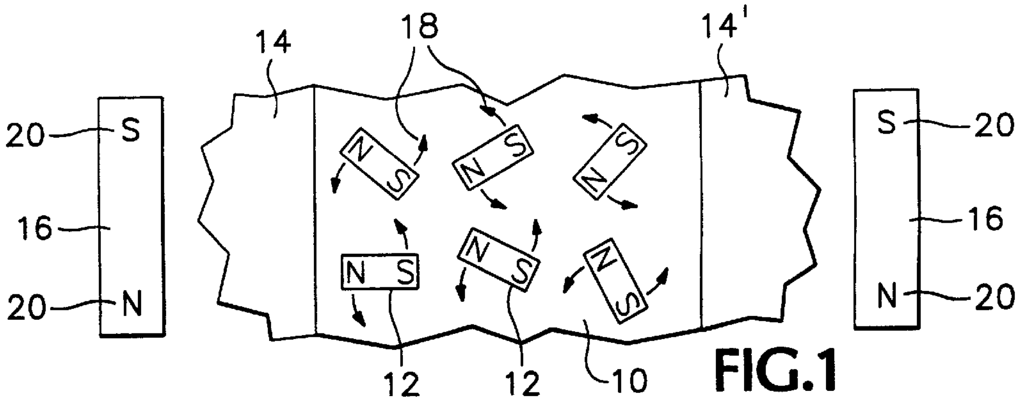
FIG. 1 is a schematic representation of a magnified cross section of two items secured together by a magnetic adhesive according to the present invention.

Referring to FIG. 1, a schematic representation of a magnified cross section of two items 14 and 14' that are to be secured together, a magnetic adhesive 10 is provided that includes plural magnetic particles 12 therewithin. Suitably, the magnetic particles are substantially homogeneously dispersed throughout the adhesive and are sufficiently small as to not substantially deteriorate the holding properties of the adhesive. The adhesive 10 is placed between surfaces of the two items 14 and 14', and holds them together (once the adhesive cures).

The introduction of the magnetic particles 12 gives the magnetic adhesive 10 several desirable characteristics. For example, an improved removal method is thereby enabled to be employed. Referring still to FIG. 1, should it be desired to separate the items 14 and 14', a magnetic field 16 is provided in close proximity to the magnetic adhesive. The magnetic particles 12 will try to align their polarities, as shown by the movement arrows 18, with the polarities 20 of applied magnetic field 16. The applied magnetic field 16 polarity 20 is then suitably continually alternated in a rapid sequence, wherein the magnetic particles 12 within the magnetic adhesive 10 will attempt to vibrate in response to the alternating field, assisting in breaking the bond of the magnetic adhesive 10 and enabling separation of the mating surfaces 14 and 14'.

While the adhesive in accordance with the present invention can be employed in many situations, preferred mbodiments of the present invention comprise adhesives, apparatus and methods for securing and removing prosthodontics. Accordingly, another embodiment of the invention is a of dental cement that contains substantially homogeneously interspersed magnetic particles 12 therein.

Figure 2:
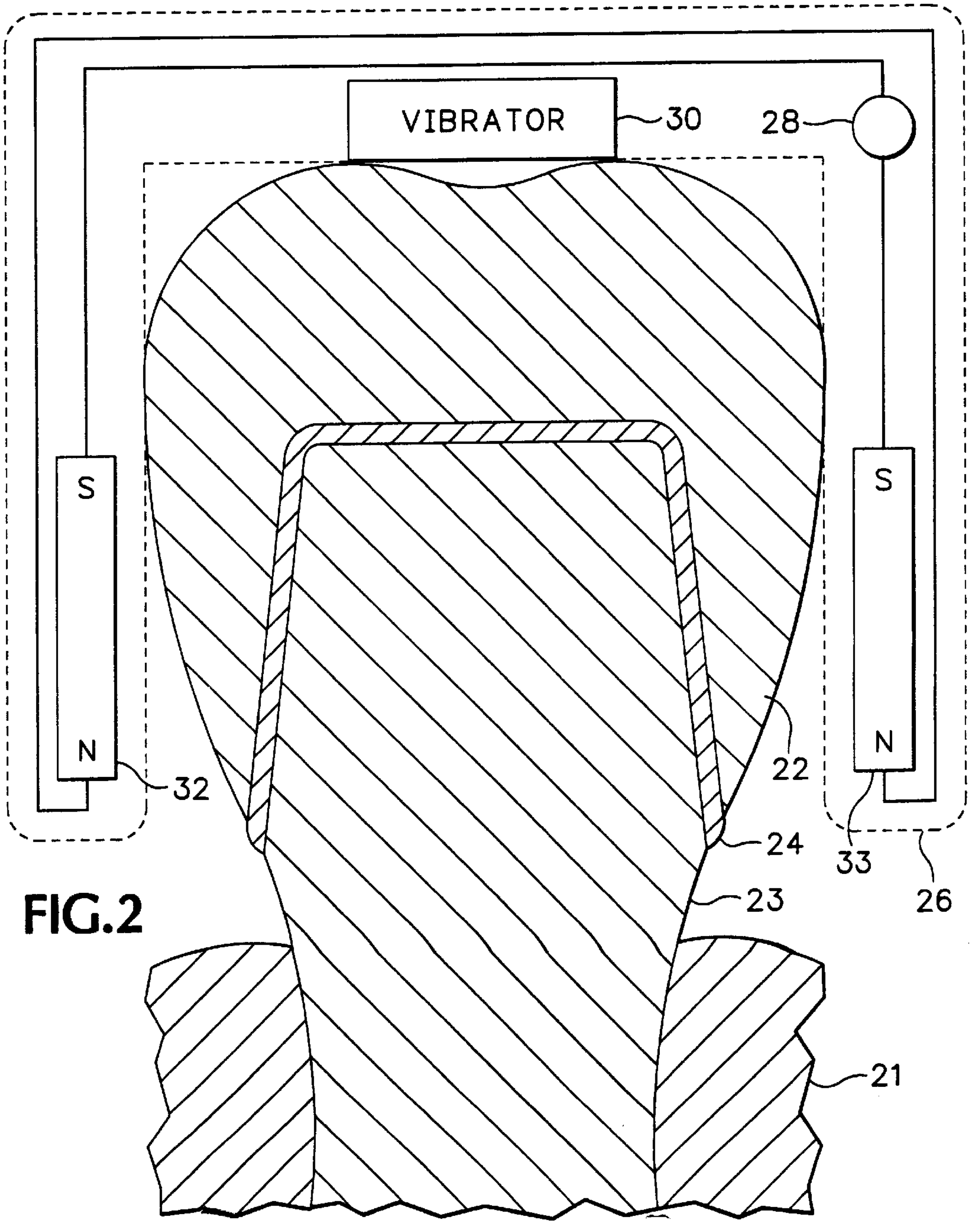
FIG. 2 is an enlarged cross section of a magnetic adhesive removable bonding system according to the present invention, as applied to a prosthodontic device.

Having employed the inventive cement to attach a prosthodontic device, the removal method differs from the prior art. Referring to FIG. 2, a cross section of a magnetic adhesive removable bonding system according to the present invention, as applied to a prosthodontic device, a prosthodontic device, such as a crown 22, is cemented into position on a base 23 (which may comprise an original tooth portion that has been reshaped to receive the crown, for example) using magnetic dental cement 24. The dental cement 24 comprises plural magnetic particles 12 therein in accordance with the embodiment of cement 10 illustrated in FIG. 1. The crown is thereby securely held in place.

However, if it should become necessary to remove the crown, an extraction tool 26 is provided, comprising first and second magnetic field generators 32 and 33, suitably positioned on opposing sides of the crown. A vibrator 30 is optionally provided, and in the illustrated embodiment, is positioned at the top of the crown. An electrical source 28 is provided and drives the magnetic field generators, suitably to generate alternating magnetic fields. To accomplish removal of the crown, extraction tool 26 is placed near or clamped onto the prosthodontic device 22 such that magnetic field generators 32 and 33 are positioned on opposing sides of the crown and alternating electromagnetic fields are produced by operation of the electrical source 28 as applied to the magnetic field enerators. Then, in the case of employing optional ibrator 30, the crown 22 is physically agitated by ibrator 30. While the removal device is operating, a twisting motion is applied by the dentist. The alternating electromagnetic fields urge the magnetic particles to move back and forth within the cement and, coupled with the vibration and twisting, will encourage the magnetic dental cement 24 to break apart.

A specific example of the extraction tool 26 comprises a wishbone shaped device that attaches to the prosthodontics and vibrates while alternating the polarity of the magnetic fields. The elements can suitably be incorporated into dental pliers so that the dentist can simultaneously apply the alternating magnetic fields and grip and pull on the crown or other prosthodontic device.

This embodiment allows for easier removal of prosthodontics and is less likely to cause physical damage. The magnetic particles may also strengthen the cement in a manner similar to that of steel rebar in concrete.

Figure 3:
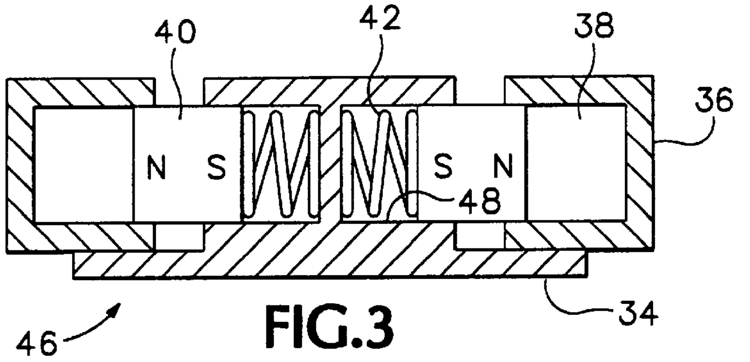
FIG. 3 is a cross sectional diagram of a locked spring loaded magnetic lock according to the present invention.
Figure 4:
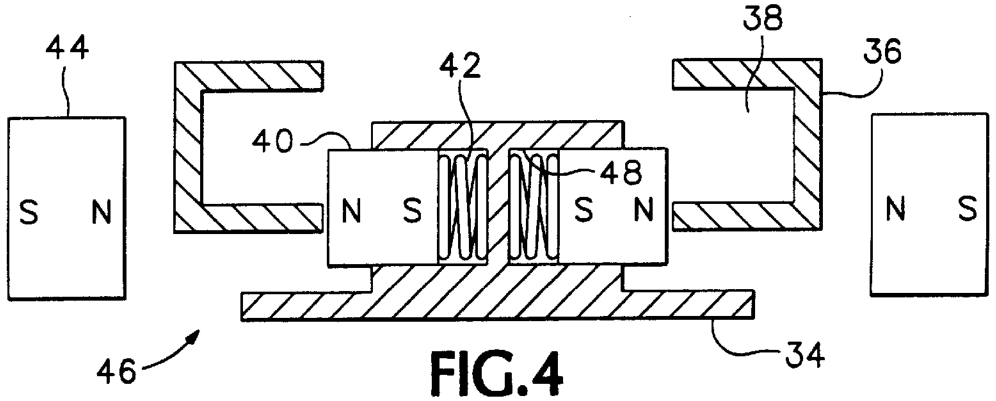
FIG. 4 is a cross sectional diagram of a disengaged spring loaded magnetic lock according to the present invention.

Referring to FIG. 3 and FIG. 4, which comprise cross sectional diagrams of an engaged and disengaged spring loaded magnetic lock mechanism according to the present invention, spring loaded magnetic lock 46 comprises a fixed component 34 housing magnetic arms 40 within internal recesses 48. Springs 42 are situated in the internal recess 48 between the innermost surfaces of the internal recesses 48 and the magnetic arms 40 so as to apply pressure forcing the magnetic arms 40 out of the internal recesses 48. In the locked position as illustrated in FIG. 3, magnetic arms 40 are forced by the bias of springs 42 into recesses 38 of a removable component 36. The shape of magnetic arms 40 conform and mate to the shape of recesses 38 of the removable component 36, thus preventing any movement of removable component 36 with respect to fixed component 34.

Referring to FIG. 4, in the unlocked or disengaged position, external magnets 44 are positioned in close proximity to magnetic arms 40 such that their nearest respective magnetic fields have identical polarities. The resultant repelling magnetic field forces magnetic arms 40 inwardly to recesses 48 and out of the recesses 38 of the removable component 36, thereby freeing removable component 36 and enabling it to be separated from the fixed component 34.

In the preferred version of this embodiment, the fixed component 34 and the removable component 36 are suitably fabricated of non-magnetic materials and the internal recesses 48 are provided, oriented approximately 180° apart. The magnetic arms 40 of the fixed component 34 are also oriented approximately 180° apart.

Figure 5:
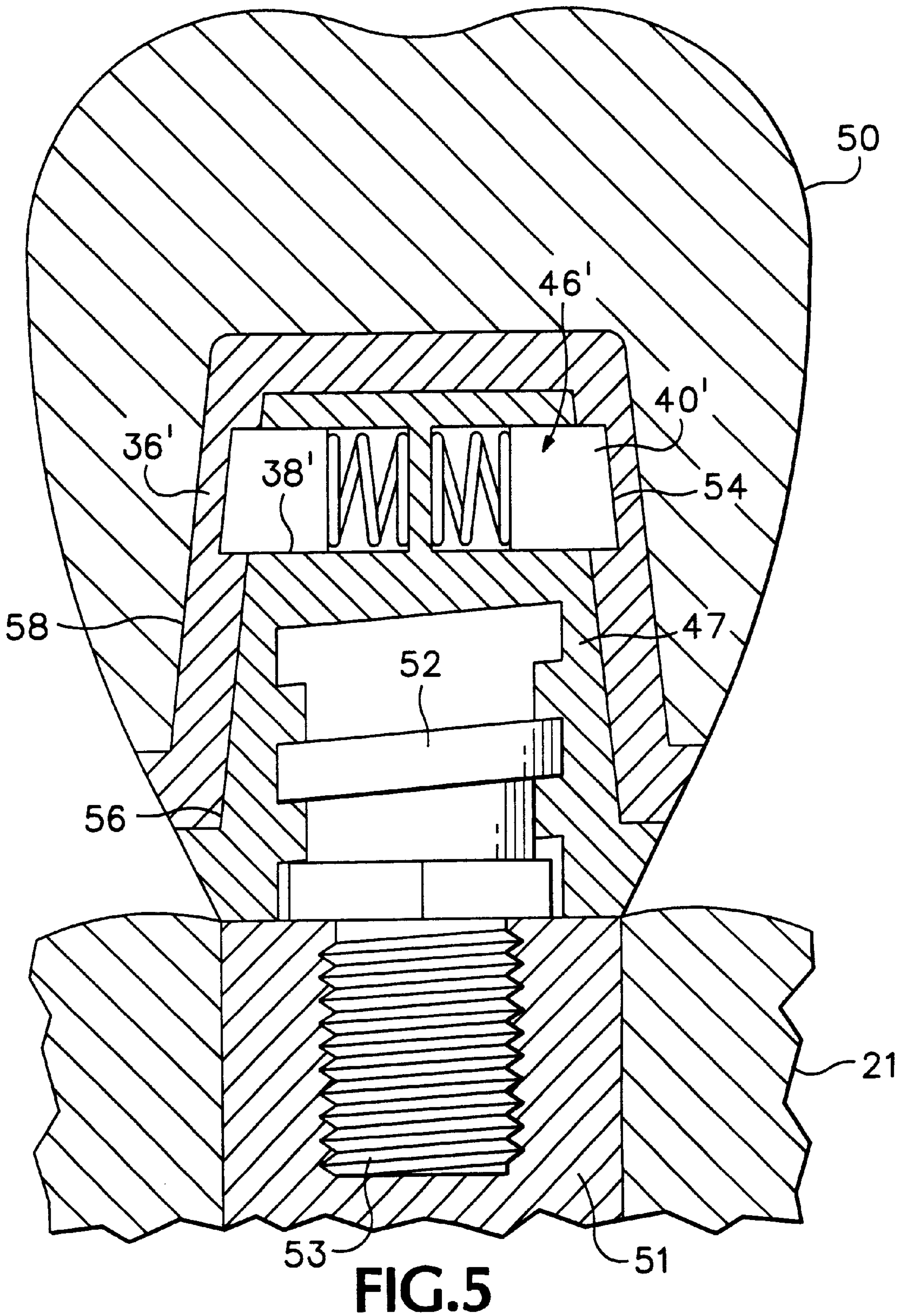
FIG. 5 is a cross sectional diagram of a locked spring loaded magnetic lock system according to the present invention, as applied to the field of prosthodontics.

An application of the embodiment of FIGS. 3 and 4 pertains to an improved apparatus and method of affixing and removing prosthodontic devices wherein a spring loaded magnetic lock affixes the prosthodontic device and a magnetic field unlocks the device. Referring to FIG. 5, a cross sectional diagram of a locked spring loaded magnetic lock system according to the present invention, as applied to the field of prosthodontics, in the locked configuration, a prosthodontic device 50 fits over an inner prosthodontic device 47, which is positioned within the mouth, and may comprise a dental implant, for example, and serves to anchor the mating crown, denture or bridge device 50 (hereinafter referred to as the outer prosthodontic device). The inner prosthodontic device 47 carries the fixed component portions of the spring loaded magnetic lock 46'. This inner prosthodontic device 47 may be aligned and attached to a tooth stub, tooth root or implant 52 using conventional dental methods. In the illustrated embodiment, a dental implant is screwed via threaded portion 53 into a tooth base 51, surrounded by gum 21 The removable component 36' is incorporated as the inner surface of the outer prosthodontic device 50. In this embodiment, the outer faces 54 of magnetic arms 40' and the body of the inner prosthodontic device 47 are tapered, narrowing from the end nearest the base point illustrated at 56. The inner surface 58 of the removable prosthodontic device 36 is tapered with a slope matching that of the outer faces 54 of magnetic arms 40 and the body of the inner prosthodontic device 47, allowing sufficient clearance for the outer prosthodontic device 50 to be slid over and attached to the inner prosthodontic device 47 without the use of magnets to repel magnetic arms 40' back into recesses 38'. Once the outer device 50 is slid into position, the springs urge arms 40' outwardly to engage with the recesses in the portion 36'.

Figure 6:
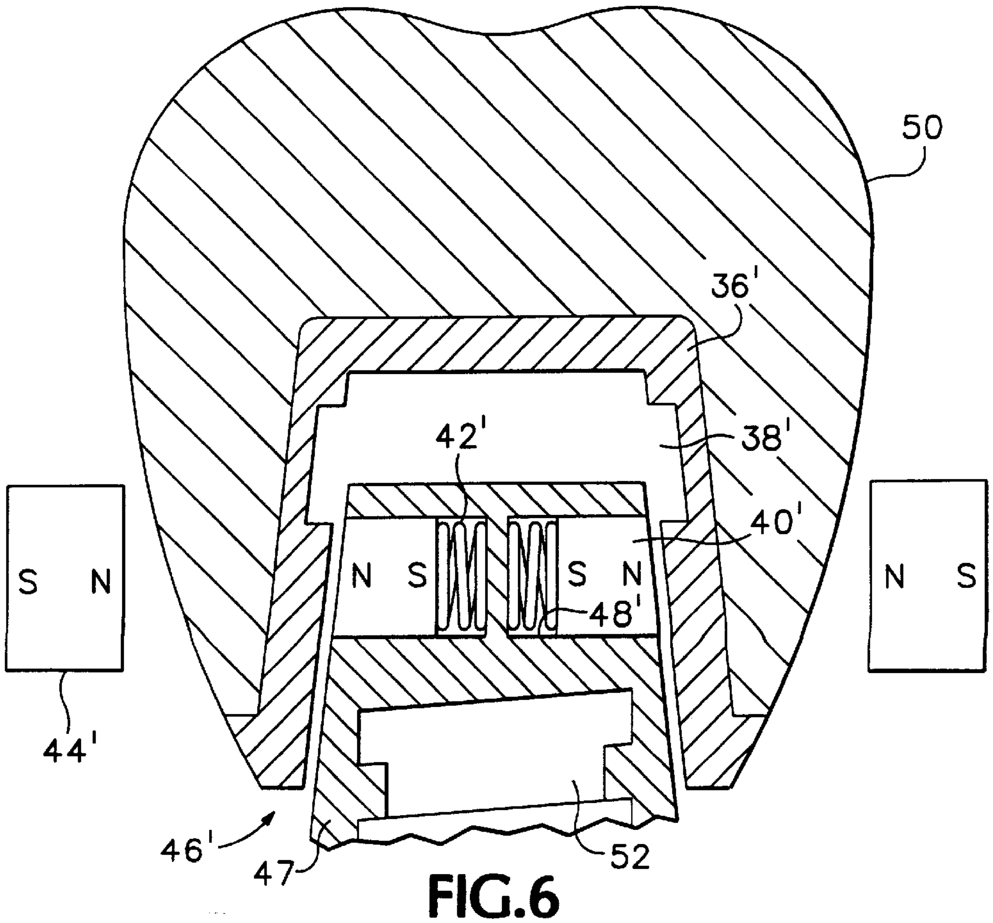
FIG. 6 is a cross sectional diagram of a disengaged spring loaded magnetic lock system of FIG. 5.

FIG. 6 illustrates a cross sectional diagram of a disengaged spring loaded magnetic lock system according to the present invention, as applied to the field of prosthodontics. The operation of the spring loaded lock 46 is as previously described hereinabove in connection with FIGS. 3 and 4. Magnets 44' are brought in close proximity to magnetic arms 40' thereby magnetically urging the magnetic arms 40' out of recesses 38' and into recesses 48', allowing a suitable clearance for removal of the outer prosthodontic device 50. Easy removal is thereby enabled, while still provided a secure engagement between the base portion and the crown portion, until removal is desired.

Accordingly, this embodiment of the invention comprises a magnetic prosthodontics removal apparatus and method for affixing and removing a prosthodontic device that uses a spring loaded magnetic mechanical lock incorporated into a part of the inner prosthodontic device that remains in the mouth. The mechanical lock has magnetic arms that are normally forced outward by spring pressure such that the arms lock into detents in the outer mating prosthodontic device. The prosthodontic devices are then magnetically separated by forcing the magnetic arms of the locking device inward against the spring tension and out of the detents by the application of a magnetic field of the same polarity. This type of quick release is especially useful to allow for ease of dentist access for performing work on the underlying inner prosthodontic device or replacement of the outer prosthodontic device.

Although a number of embodiments described herein are directed towards use in dental applications, in a broader sense the magnetic locking device can be used in numerous other situations requiring mechanical locks. This style of magnetic lock is especially well suited to applications where a key is not desirable or where access to the lock is an issue. The magnetic particles can be interspersed in other cements, glues and adhesives for use of this system outside the field of dentistry. The breakup of bonds in such cements, glues or adhesives may be accomplished by the use of alternating electromagnetic field devices with or without an applied vibration.

While plural embodiments of the present invention have been shown and described, it will be apparent to those skilled in the art that many changes and modifications may be made without departing from the invention in its broader aspects. The appended claims are therefore intended to cover all such changes and modifications as fall within the true spirit and scope of the invention.

What is claimed is:

1. A system for the non-destructive adhesion and separation of items comprising:

an adhesive medium containing a plurality of magnetic particles dispersed therein; and a magnetic field generator for assisting in release of said adhesive medium from the items; and at least two arms carrying said magnetic field generator on at least one of said arms, wherein said arms are adapted for contacting at least one of the items and exerting pressure thereagainst so as to form a clamping device.

2. The system for the non-destructive adhesion and separation of items according to claim 1, wherein said adhesive medium comprises a cement.

3. The system for the non-destructive adhesion and separation of items according to claim 1, wherein said adhesive medium comprises a glue.

4. The system for the non-destructive adhesion and separation of items according to claim 1, wherein said adhesive medium comprises an adhesive tape.

5. The system for the non-destructive adhesion and separation of items according to claim 1, wherein said adhesive medium comprises a dental cement.

6. A system for the non-destructive adhesion and separation of items comprising:

an adhesive medium containing a plurality of magnetic particles dispersed therein;

a magnetic field generator for assisting in release of said adhesive medium from the items;

at least one arm carrying said magnetic field generator thereon, wherein said arm is adapted to be positioned in a substantially close proximity to at least one of the items that are bonded together by said magnetic adhesive medium; and a vibrator to vibrate said at least one arm.

7. The system for the non-destructive adhesion and separation of items according to claim 6, wherein said adhesive medium comprises a cement.

8. The system for the non-destructive adhesion and separation of items according to claim 6, wherein said adhesive medium comprises a glue.

9. The system for the non-destructive adhesion and separation of items according to claim 6, wherein said adhesive medium comprises an adhesive tape.

10. The system for the non-destructive adhesion and separation of items according to claim 6, wherein said adhesive medium comprises a dental cement.

11. A method for the non-destructive bonding and separation of surfaces comprising the steps of:

bonding together at least two surfaces utilizing an adhesion medium with a plurality of magnetic particles dispersed therein;

positioning at least one magnetic field of oscillating polarity in a substantially close proximity to said bonded surfaces, thereby causing movement of the magnetic particles in the adhesive medium so as to aid in the non-destructive separation of the surfaces, wherein said surfaces to be bonded together comprise prosthodontic devices.

12. A method for the non-destructive bonding and separation of surfaces comprising the steps of:

bonding together at least two surfaces utilizing an adhesion medium with a plurality of magnetic particles dispersed therein;

positioning at least one magnetic field of oscillating polarity in a substantially close proximity to said bonded surfaces, thereby causing movement of the magnetic particles in the adhesive medium so as to aid in the non-destructive separation of the surfaces, wherein said positioning step further comprises the steps of:

clamping an apparatus comprising at least two arms with oscillating magnetic fields generators thereon adjacent the bonded surface to be separated;

activating said oscillating magnetic fields; vibrating said surfaces to aid the separation of the surfaces; and manipulating the clamping apparatus to further aid in the non-destructive separation of said surfaces.

13. A prosthodontic magnetic locking device comprising:

a first surface with at least one biased magnetic arm having a first profile wherein said first surface is a first prosthodontic device adapted to be anchored in a mouth; and a second surface with at least one region with a second profile corresponding to said profile of the biased arm wherein said second surface is a removable prosthodontic device, and wherein said magnetic arm is biased so as to abut said first profile to said second profile to prevent said first surface from moving relative to said second surface.

14. The prosthodontic magnetic locking device of claim 13 wherein the number of said arms is two and the number of regions on said second surface with profiles corresponding to said profiles of said arms so as to form catch receptacles is two, and wherein said arms comprise springs wherein said arms activate by said springs so as to latch into said catch receptacles.

15. The prosthodontic magnetic locking device of claim wherein said magnetic spring activated arms of the first surface are oriented approximately 180° apart.

16. A system for removably locking at least two elements together comprising:

a first surface defined in a first of said at least two elements comprising at least one magnetic spring activated arm having a first profile;

a second surface defined in a second of said at least two elements comprising at least one receiver corresponding to said first profile of the spring activated arm; and an unlocking device comprising at least one magnet, wherein said arm is adapted to engage said receiver so as to lock said first surface and said second surface together, and to disengage from said receiver in response to said unlocking device, wherein said elements to be removably locked together are prosthodontic devices.

17. The system according to claim 16 further comprising:

at least a second magnetic spring activated arm defined in said first element and having a second profile;

at least a second corresponding receiver having a complementary profile to the second profile of the at least second spring activated arm.

18. A method for the non-destructive locking and non-destructive separation of two surfaces comprising the steps of:

engaging a first surface with a magnetic spring activated arm having a profile with a corresponding detent on the second surface matching said profile of the spring activated arm, wherein said detent receives said arm so as to lock the surfaces from moving relative to each other;

positioning at least one adjustable arm with a magnet attached thereon in a substantially close proximity to the locked surfaces, thereby urging said magnetic arm to disengage from said detent; and physically separating the surfaces, wherein said surfaces comprise portions of prosthodontic devices.

* * * * *